(12) United States Patent
Hein et al.

(10) Patent No.: US 10,180,400 B2
(45) Date of Patent: Jan. 15, 2019

(54) DEVICE FOR DIGITAL READING OF QUICK TESTS

(71) Applicant: OPTRICON ENTWICKLUNGSGESELLSCHAFT FÜR OPTISCHE TECHNOLOGIEN MBH, Berlin (DE)

(72) Inventors: Wilko Hein, Berlin (DE); Grigorios Barboutis, Berlin (DE)

(73) Assignee: Optricon Entwicklungsgesellschaft Fur Optische Technologien MBH, Berlin (DE)

( * ) Notice: Subject to any disclaimer, the term of this patent is extended or adjusted under 35 U.S.C. 154(b) by 41 days.

(21) Appl. No.: 14/912,695

(22) PCT Filed: Aug. 18, 2014

(86) PCT No.: PCT/DE2014/000433
§ 371 (c)(1),
(2) Date: Feb. 18, 2016

(87) PCT Pub. No.: WO2015/024553
PCT Pub. Date: Feb. 26, 2015

(65) Prior Publication Data
US 2016/0202190 A1 Jul. 14, 2016

(30) Foreign Application Priority Data
Aug. 20, 2013 (DE) .................... 10 2013 014 059

(51) Int. Cl.
*G01N 21/77* (2006.01)
*G01N 21/84* (2006.01)
*G01N 21/78* (2006.01)

(52) U.S. Cl.
CPC ......... *G01N 21/8483* (2013.01); *G01N 21/78* (2013.01); *G01N 2021/7759* (2013.01); *G01N 2201/125* (2013.01)

(58) Field of Classification Search
None
See application file for complete search history.

(56) References Cited

U.S. PATENT DOCUMENTS

| 5,622,871 A | 4/1997 | May et al. |
| 9,243,997 B2 | 1/2016 | Petruno et al. |

(Continued)

FOREIGN PATENT DOCUMENTS

| EP | 1 582 598 A1 | 10/2005 |
| EP | 2 385 369 A1 | 11/2011 |
| WO | WO 2010/054645 A2 | 5/2010 |

OTHER PUBLICATIONS

International Search Report (PCT/ISA/210) dated Feb. 10, 2015, by the European Patent Office as the International Searching Authority for International Application No. PCT/DE2014/000433.

(Continued)

*Primary Examiner* — Jill A Warden
*Assistant Examiner* — Brittany I Fisher
(74) *Attorney, Agent, or Firm* — Buchanan Ingersoll & Rooney PC (57) ABSTRACT

A device for photometric qualification of lateral flow quick tests by means of camera imaging includes an arrangement which manages with a pinhole aperture with a slot-shaped opening, which has been integrated into the basic housing body, in which the imaging has been optimized with a view to diffraction, imaging scale and integration behavior and in which the illumination and all the components are arranged in a housing which can be produced at a reasonable price, with the result that the quantifiability of customary LFA quick tests is made possible for the user with a sufficient (Continued)

precision. The device can transmit test-specific data automatically and contact-free with the help of electromagnetic waves via a transponder (RFID) and is thus suited for various tests and for quantification of LFA's. The device may work autonomously with an internal microcontroller (embedded system). The figures can be stored and optionally transmitted to a computer via an interface.

10 Claims, 12 Drawing Sheets

(56) References Cited

U.S. PATENT DOCUMENTS

| | | | |
|---|---|---|---|
| 9,989,527 B2 | 6/2018 | Petruno et al. | |
| 2004/0241752 A1 | 12/2004 | Anderson et al. | |
| 2005/0095697 A1 | 5/2005 | Bachur et al. | |
| 2005/0201898 A1* | 9/2005 | Borich | G01N 21/78 422/82.05 |
| 2008/0237476 A1* | 10/2008 | Uribe | G01T 1/1611 250/363.04 |
| 2010/0267049 A1 | 10/2010 | Rutter et al. | |
| 2010/0315644 A1* | 12/2010 | Egan | G01N 21/8483 356/445 |
| 2011/0293153 A1 | 12/2011 | Plickert et al. | |

OTHER PUBLICATIONS

Written Opinion (PCT/ISA/237) dated Feb. 10, 2015, by the European Patent Office as the International Searching Authority for International Application No. PCT/DE2014/000433.

* cited by examiner

DEVICE FOR DIGITAL READING OF QUICK TESTS

BACKGROUND OF THE INVENTION

Field of the Invention

The invention relates to a device for digital reading for quick tests, in particular for photometric assessment of a test strip, a so-called lateral flow assay (LFA). Such LFA's are increasingly being applied as quick tests, the invention can thus be used in diagnostics and also in bio-analysis.

Background of the Related Art

There is an increasing need for objective and decision-safe aids in evaluation, especially measurement devices for self-users of quick tests with intuitive use/operation, which have to be constructed simply and can be added to test packs (e.g. in pharmacies). They should possibly also be suited for single use (so-called disposables). In devices for professional use, camera-based devices have proven their superiority with a view to precision, reproducibility and mechanical robustness. However, the high technical efforts and the costs have made use in the final consumers' area more difficult up to now. In addition, professional devices require batch- and test-specific calibration data for the measurements, which appears difficult up to now in favourably priced systems.

In bio-analysis, immunoassays are amongst the most frequently used methods, because they enable fast diagnostic prognoses, sequence controls of disorders, detection of toxins or monitoring of medication in the body with low efforts, costs and time.

The LFA's (test strips) are based on the principle that a small quantity of the sample fluid to be examined is put into contact with marked antibodies at the sample application point. If a sufficient quantity of the analyte exists in the sample fluid, it can react with the marked antibody and form an immune complex. On a membrane, further immunological components have been fixed in a line at defined points (test line), recording either the free or the complexed marked antibodies from the sample and thus augmenting a photometrically measurable signal (colour of the gold particles) on these lines. Whereas a qualitative statement and a visual (subjective) assessment of the test bands without a measurement device is sufficient for interpretation of some analytes (pregnancy test), objective and reproducible or, if applicable, quantitative signal evaluations with a matching measurement device are necessary for other analytes. The trend is using devices for objectification of the statements, even in qualitative tests.

Figure 9:
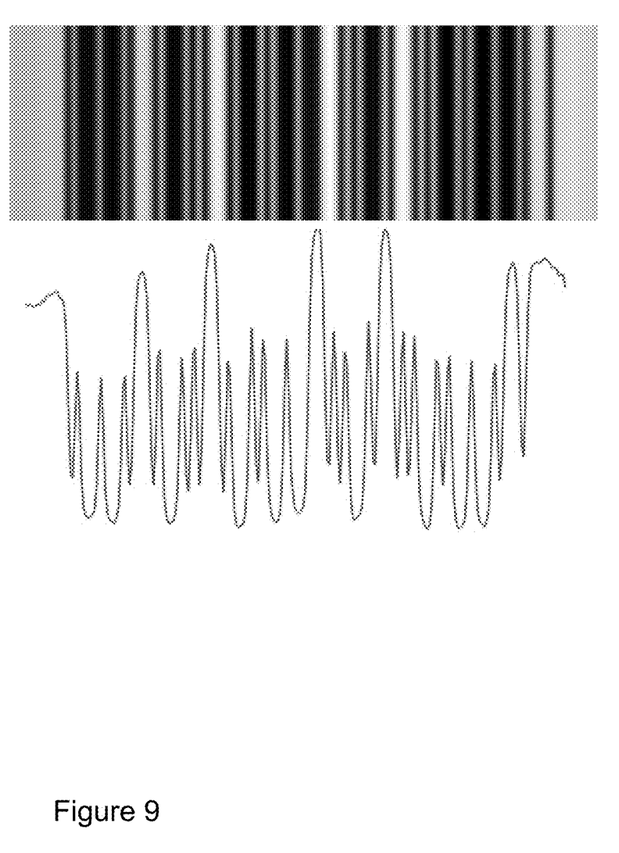
FIG. 9: image and grey level scan for a barcode.

Such test strips are installed in test cassettes (FIG. 9). A sample fluid, for example blood, urine or saliva in the event of a diagnostic quick test, is applied to an opening in the test cassette provided for this purpose, there is an antibody reaction of the strip, subsequently there is discoloration in two strips in the observation window of the test cassette. The discoloration of the test line gives information about the concentration of the analyte, control line C displays the validity of the test. Such quick tests are increasingly being used in human diagnostics, in the analysis of foodstuffs (mycotoxins), in drug analysis and in allergy diagnostics.

Originally, these quick tests were developed for simple yes/no answers, for example for a pregnancy test. With the increase in technical progress, these tests have been designed to be increasingly quantifiable, i.e. the amount of the change of colour correlates with the concentration of the analyte and thus enables statements about the severity of an incident. At the beginning, the manufacturers of the tests enclosed colour tables in the test packaging as evaluation aids for the consumers. On the basis of these coloured pictograms, the test users were to be able to assess the result with a view to the colour intensity and thus establish the outcome. For professional use, devices for quantitative assessment of these tests were developed, so-called readers. In such readers, the assessment is done on the basis of batch- and test-specific calibration curves which have been recorded in the appliance and with which the measured value is electronically compared. Due to the complex technical problems and the necessary precision, such devices are however too complicated for final consumers.

As a rule, the final user buying a self-test in a pharmacy still has to have recourse to colour tables enclosed with the sales packages. But the end user often feels unsure when evaluating personally and would like an unambiguous, legible statement not containing any uncertainty for the decision. On the market, simple devices designed for a final user only exist for selected tests for the evaluation of tests, for example for pregnancy tests or for selected tests in the USA.

The functional common point for all evaluation devices is that the test strips are illuminated and the reflected light is assessed photometrically in a defined pixel grid. For this, line-shaped (one-dimensional) or areal (two-dimensional) scans are held in the test field and the light intensity of each pixel (image point) is measured and stored digitally. From the amount of the reflection signal of the test line, the concentration of the analyte in the sample is determined via the calculatory comparison with a calibration curve stored in the memory and displayed.

Professional devices in laboratory use known according to the state of the art work either according to the scanner or the camera principle. In the scanner principle, the transmission and reception units are in a very close grid (as a chip) at a small distance from one another. In the relative movement between the object to be portrayed and the transmission and reception unit, an optomechanical process, the object is scanned according to the defined grid and electronically recorded as an image. Scanners are frequently mechanically susceptible, but available at a favourable price in large quantities. With the camera principle, the object is read electronically onto a photo-receiver with a large quantity of reception pixels, e.g. a CCD matrix or line, by means of an optic and evaluated. The benefits of the camera principle are its mechanical robustness and the quick imaging. Recording of images at a defined frequency makes film recordings possible.

On the other hand, good camera systems are rarely available at a favourable price. With cheaper camera-based evaluation systems, the user additionally buys simple and cheap webcams and processes the images with conventional operating systems. Due to the unreliable white balance and the susceptibility of the complex software (e.g. in the use of Windows image processing software), these systems are not reliable.

In European patent application 09820077.7-1524 "Device and Method for Evaluation and Assessment of a Test Strip", a solution is proposed in which the image is read directly from the CCD matrix by a microcontroller. In the visual area of the camera, there are colour-stable calibration normals according to the invention, with which the device is calibrated at each start of the device. The test- and batch-specific data have been stored on a matching SD card, a barcode scanner checks the test identity on the reverse of the test cassette and thus rules out confusion of tests.

The disadvantage of these devices is the high technical efforts connected with them. Precise recording demands a high-quality optic, a complicated CCD matrix and a 32-bit processor with additional storage possibilities.

There are the following technical approaches to solutions for final customers' self-tests, which have the same objective of carrying out an assessment with the lowest possible number of optical components.

One group of these approaches to solutions proposes only using individual photo diodes for evaluation if possible. For example, in the pregnancy test (U.S. Pat. No. 5,622,871), both the control line and the test line are recognised with individual PIN photodiodes for evaluation of the test fields. In the evaluation, these photodiodes have no relative measurement variable, but provide a simple yes/no answer. The selling company advertises with the fact that ¼ of the women err in evaluation without a measurement device, which can be ruled out with the electronic display.

From EP 2385369A1, an assay reader is known, which is sold under the name of "Alverix" and has only been provided with a source of light and a photodiode. The device manifests a shaft, into which the test cassette is inserted for measurement. With this device, a line-shaped scan is generated at a right angle through test and control line by the relative movement during the insertion of the test into the measurement shaft. For this, a one-dimensional scan is generated through the observation window of the cassette with only one illumination element (LED) and one photodiode along the diode. The disadvantage with this solution is that no local information can be assigned, only one relative image can be evaluated on the basis of the scan, i.e. the maxima can be placed in relation to one another or to the basic figure. A further essential disadvantage is that the precision of the scan and the figures depends on the insertion speed of the operator. If the test is inserted at high speed, the photodiode has to measure very quickly, which can lead to false measurements.

All immunoassay tests on the market have differing test sequences. This means that the degree of change of colour may be reproducible as a function of the analyte concentration, but also follow various mathematical functions. As a rule, they are very similar to the Rodbard function (the more analyte, the stronger the discoloration or change of colour). In so-called competitive assays, the discoloration is inverse (discoloration drops with a high concentration). In addition, the parameters of the functions may change with differing batches. This means that measurement devices for the quantification of differing immunoassays must be in a position to identify the tests and/or that test-specific calibration data have to be added. In the devices available on the market, this is implemented either with a manual input or via a scanner or a barcode on the reverse.

BRIEF SUMMARY OF THE INVENTION

Embodiments of the invention may have one or more of the following properties:
- acts as an electro-optically supported measurement device for LFA quick tests for final users,
- uses the advantages of a camera system and can nevertheless be produced at a favourable price,
- only comprises a small number of components,
- can be produced at such a favourable price that it can be placed in the packaging for use by the test user,
- nevertheless has the functionality of a mobile evaluation device to a great extent,
- is to be usable for a test in a period which can be determined beforehand,
- can evaluate arbitrary tests by addition of one or more piece(s) of specific information,
- is to be configurable for various applications, i.e. various tests with various curves, and is thus to be suited not only for qualitative tests, but also for quantification of immunoassays.

Using the advantages of a camera-based system means generating one-off images of the test strips, repeatedly in succession as far as possible. Use must be made of a source of light which illuminates the object to be portrayed sufficiently. Imaging is implemented on a receiver with a number of reception elements (pixels). The evaluation function of the images should be combined with an embedded system in one device or be added to the device directly before the measurement. The values are to be storable and, if so required, readable with an adapter. The measurement device should be constructed so simply that if applicable it can be enclosed with a packaging unit for one-off use. The measurement device should be able to evaluate any number of lines in the test field and also test fields located close to one another.

The core of the invention is the realisation of a simple camera as a component working autonomously, which is intuitively placed above the test field by the user, supplies an objective outcome and makes use of the benefits of a camera system. It has been found that the simple measurement and display device can achieve measurement precision and resolution in customary quick tests approaching that of professional readers.

BRIEF DESCRIPTION OF THE FIGURES

FIG. 10: schematic set-up of an LFA
FIGS. 11 a and b: test cassette with transponder The following is a list of reference numbers appearing in the Figures:
(1) Test cassette
(2) Opening for insertion of the test sample
(3) Inspection opening for test evaluation
(4) Test line ("capture line")
(5) Control line
(6) Basic housing body
(7) Added part
(8) Recess on underside of the basic housing body
(9) Lid for battery compartment
(10) Groove for opening of the battery compartment
(11) Display
(12) Operating element (push button)
(13) Mini USB plug
(14a and 14b) Markings on the test cassette
(15) Arc-shaped, half-moon-shaped section
(16) Axis of the optical imaging
(17) Underside of the measurement device
(18) Flexible tongue (19) Pinhole aperture with slot-shaped opening (slot aperture)
(19a) Pinhole aperture in the body
(20) Lens
(21) Battery compartment
(22) 3 Lithium diode cells
(23) Electrical wiring carrier, preferably circuit board
(24) Reception element, CCD reception cell
(25) Optical axis for illumination
(26) LED
(27) Display
(28) Housing recess of the basic body
(29) Signal transmitter
(30) Signal from the test line
(31) Signal from the control line
(32a) Peak height, grey level test line
(32b) Peak height, grey level control line
(A) Sample pad
(B) Antibody pad
(C) Control line
(D) Suction pad
(E) Test line
(F) Nitrocellulose membrane
(33) Transponder
(34) Aperture body

DETAILED DESCRIPTION OF THE INVENTION

The appliance according to the invention for digital measurement for quick tests comprises a basic housing body, an added part, a source of light, optical components for the recording (pinhole aperture), a CCD line as a receiving element, an electronic circuit (circuit board), a display component, an electrical interface for data transmission, a cable/contact-free data transmission system, a support device for the quick test, a current supply and an operating element (switch).

A typical device according to the invention is characterised by the fact that
- a pinhole or slot aperture serves as an imaging element and additional optical components (lenses) are done without,
- the slot aperture has been arranged parallel to the lines to be detected,
- the slot aperture has been integrated in the basic housing body for reproduction and additional positioning of the optical components can be done without,
- the test-specific data are transmitted between the test and the evaluation device via a cable/contact-free automatic identification with the help of electromagnetic waves (so-called RFID: Radio Frequency Identification). For this, a transponder, on which the test-specific data inquired wirelessly by the reading device have been recorded, is located on the reverse of the test or on the test packaging,
- the test results can be stored off on the transponder located in the test One advantage is that the wavelength of the source of light can be adapted to the test.

The possibility of accommodation (battery compartment) for the energy supply has been fitted in the basic housing body 6.

The inner surface is designed such that it is optically inactive. This is achieved by the inner surface being matted. Another possibility of designing the surface optically inactive entails implementing the lateral illumination at such an angle that no disturbing reflections result.

The electro-optical measurement device according to the invention works according to the camera principle, in which a favourably priced CCD line is used, containing a microcontroller for evaluation and an LED for illumination, in which all the elements have been arranged in one unit of only 2 housing bodies and which simultaneously has independent control of the measurement sequence.

An essential feature of the invention is the use of a pinhole aperture with a slot-shaped opening for reproduction of a strip pattern on the line sensor, a so-called anamorphous optic.

A pinhole aperture would be sufficient for imaging. But with the use of a slot aperture, the slot of which is parallel to the test strips, the brightness of the image on the sensor is increased by a factor of 5. As a result of the slot aperture, a greater width of the test lines is projected onto a pixel of the CCD line, the brightness and the measurement dynamism and measurement precision are increased. With the use of the slot aperture, an integration effect across the width of the strips is achieved and the imaging becomes less sensitive to inhomogeneities in the test lines.

Despite the use of the CCD lines, the information content of the entire contents of the surface of a test strip can be read off and evaluated through the slot aperture.

Further, a battery, a triggering button and a display have been fitted in this unit. The entire measurement device works autonomously. The underside of the device manifests an opening, which is intuitively placed on a measurement window for the measurement process. The test cassette and the measurement device each have corresponding geometric structures, making it possible for each user to place the test at the right measurement position intuitively. The measurement is triggered by a key switch. The measured value is displayed after only a few seconds.

The housing comprises two parts. In one part of the housing, an aperture and, if applicable, a lens have been arranged in an optical axis vertical to the object to be measured. The distances between the main lens axis or the aperture and the object to be measured or the CCD have been dimensioned such that an optimal portrayal of the measurement window to the CCD line is guaranteed. In this basic body, there is a chamber to take the battery. In addition, the body manifests an opening to take illumination, which guarantees that the sample is illuminated from the side. The lateral illumination is done at such an angle that reflections from the surface of the measurement sample (for example in the case of use of tests protected by a transparent film or a window) do not reach the receiver.

The basic body manifests a stopping face on which a wiring carrier, preferably a circuit board, has been fitted. The circuit board manifests the CCD sensor, a microcontroller, the transmission/reception units for the cable/contact-free data transmission and, if applicable, a plug as the central construction elements.

All the housing bodies have been constructed such that they can be manufactured in large quantities by injection moulding technology.

Advantages of the Device According to the Invention

The advantages result from the implementation of the camera solution with preferred dimensions of approx. 40×40×40 mm$^3$ and a low mass of approx. 80 g. With a camera, pictures can be taken within a fraction of a second. The microcontroller reads this pixel information from the CCD cell (or matrix) within a short period of time. Thanks to taking a number of pictures within a short interval of time, higher measurement precisions can be achieved than with one-off scanning according to the optomechanical principle. Further, image sequences can be taken during the test development, with which forecasts about a final result to be expected can be made with known sequences of discoloration in tests. For example, if a complete test lasts for 15 minutes until "total development", statements about a final result to be expected can be made after only a few minutes by the evaluation of image sequences. The use of the test dynamism is particularly promising if, for example, only one line and thus not many values are to be processed in a system.

By the use of 2 standard LED's, a relatively homogeneous illumination of the test field is achieved.

Although no additional, optically imaging construction elements have to be used and only a pinhole aperture with a slot-formed opening, which is fixed in the basic housing body in the manufacturing process, is used, a high-quality optical imaging is achieved. Thanks to the slot-shaped opening of the pinhole aperture parallel to the test line, an integration effect is achieved and imaging is less sensitive towards inhomogeneities within the test line. Whereas a classical pinhole aperture would provide an imaging behaviour which is similar in all directions of the image level, the resolution parallel to the test strip is reduced by the slot-shaped embodiment, in order to generate the required integration effect. A further benefit of the slot aperture is the increase of the useful signal reaching the sensor, as a result of which the signal-to-noise ratio is simultaneously improved.

For reasonably priced measurement devices for final users, the batch-dependent calibration can be waived in certain tests. In the memory of the measurement device, absolute figures are stored by the manufacturer as comparative values and decision thresholds. The embodiment of the device according to the invention additionally provides possibilities of identification and configuration of various tests and of automatic and contact-free transmission of batch-specific test data with the help of electromagnetic waves (preferably by means of RFID). For this, a transponder, from which the test-specific data are automatically read into the device by the electronics in the device via electromagnetic waves, can be fitted to the test or onto the packaging unit.

If the test has been fitted with a transponder, there is the possibility of recording the test outcomes established directly on the test through the measurement device.

As the system is controlled by a microcontroller, there is the possibility of storing the measured values. Thanks to a simple interface cable, the values can be read off and transmitted to an external computer.

Below, the Invention is Explained in More Detail with a Number of Figures.

Figure 1:
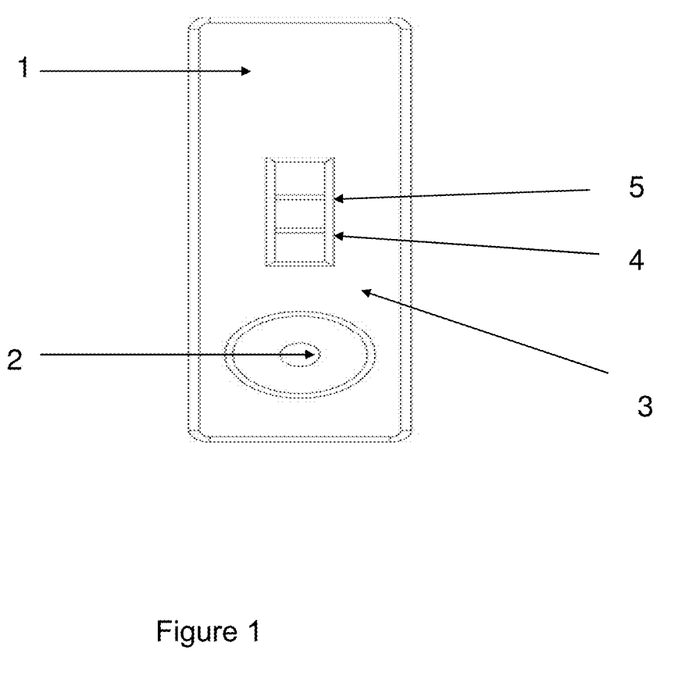
FIG. 1: is a test cassette

In FIG. 1 a test cassette (1) is portrayed. In the test cassette, there is a test strip of an absorbent fleece. The cassette manifests no less than two openings. In opening (2), a test fluid (for example blood or saliva) is applied. This fluid spreads across the test strip and flows in the direction of the observation opening (3). On the strip, vertical to the flow direction, reagents have been applied in strip-shaped lines, in which a change of colour reaction comes about. A first line (4), "capture line" displays the concentration of the analyte to be detected, the second line, the control line (5), shows the validity of the test.

Figure 2:
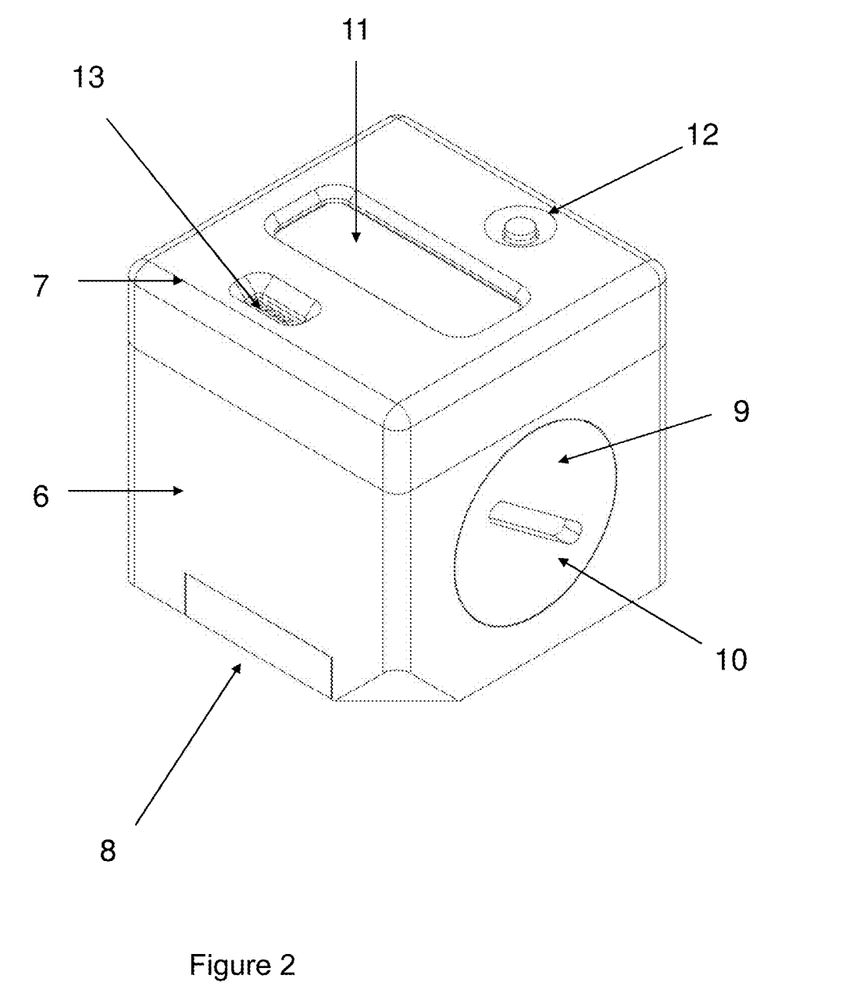
FIG. 2: measurement device in a perspective view

In FIG. 2, the electro-optical measurement device is portrayed in a perspective view. The device comprises two housing parts, a basic housing body (6) and an added part (7). On its base, the basic housing body manifests a recess (8), the shape of which corresponds with that of the test cassette. The depth of the recess matches the height of the test cassette. On one side of the housing, there is an opening as access to the battery compartment, which is closed with a lid (9). The lid manifests a groove (10) for a tool, with which the lid can be fixed or removed, as a case may be, by a screw movement.

The upper side of the added part (7) contains openings for a display (11), a push button (12) and a plug (13).

Figure 3:
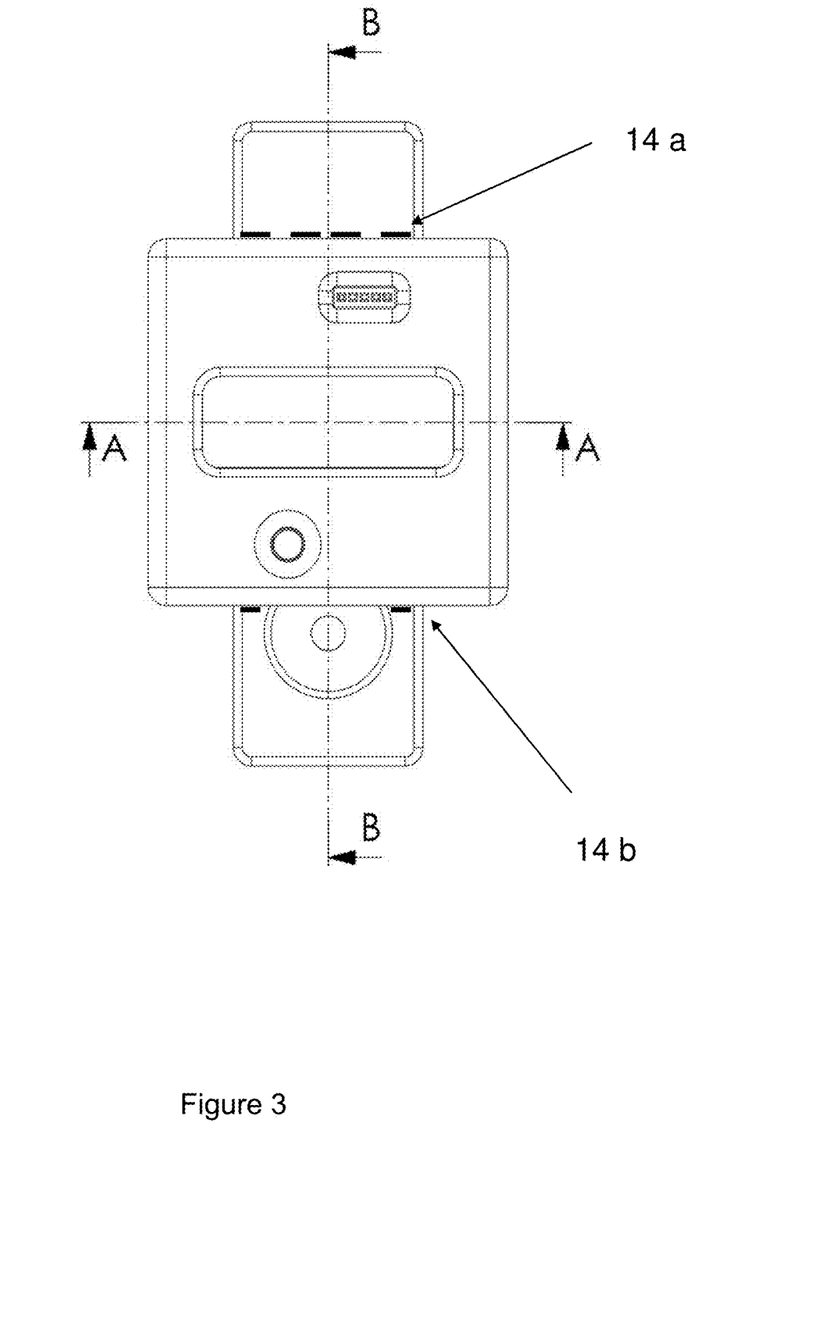
FIG. 3: measurement process with measurement device and top view with test cassette

FIG. 3 shows the measurement process perspectively. The measurement device is placed on the observation opening (3) of the test cassette. In this, the camera of the measurement device is positioned precisely above the observation opening. For the correct position, either markings on the test cassette (14*a* and 14*b*) or corresponding geometrical structures between test cassette and measurement device can be used, for example stops or milling grooves on the test cassette.

Figure 4:
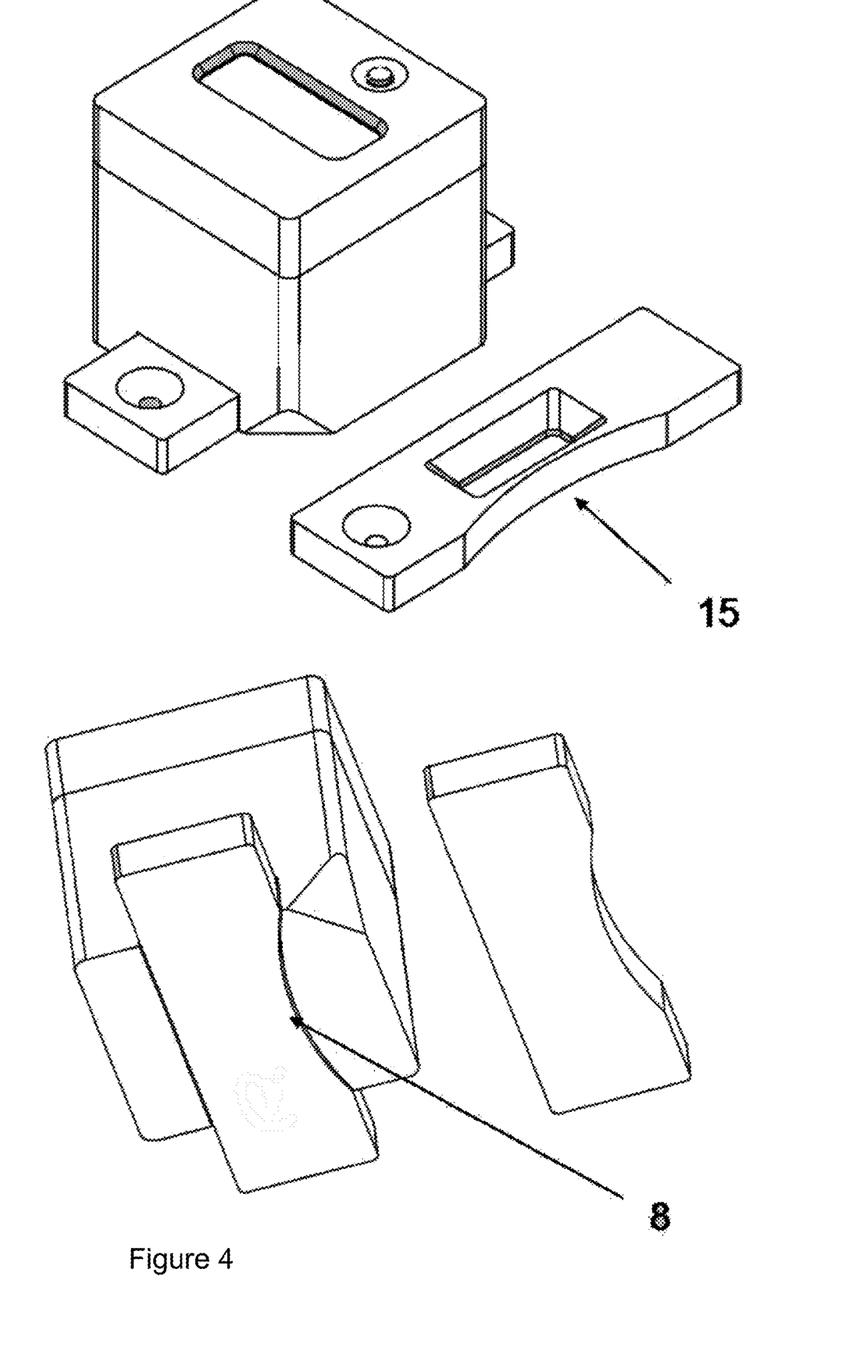
FIG. 4: cassette and section with arc-shaped section

FIG. 4 is an exemplary portrayal of a cassette with a contour, in which the position of the measurement device is unambiguously determined. The test cassette manifests an arch-shaped section (15). The recess on the base has been shaped such that the cassette can only be inserted here in an unambiguous position. Thanks to this contour, the measurement device can be positioned intuitively, it is unambiguously fixed and cannot slip relative to the measurement field. The concave section can also be shaped convex, with the result that the cassette is broader in the middle and the recess on the base has been adapted to it.

Figure 5:
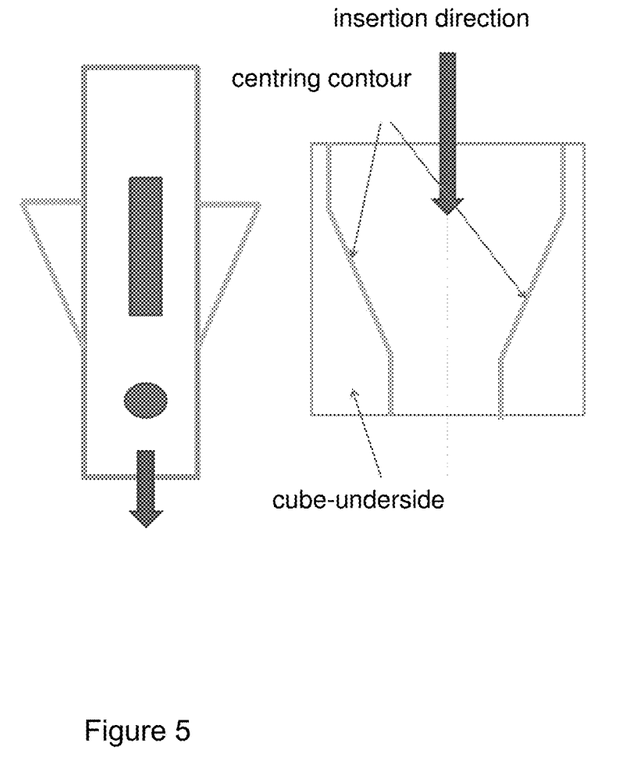
FIG. 5: cassette and section with triangular guidance contour

As an alternative, as shown in FIG. 5, the cassette can also have two triangular lateral wings, which correspond with a centring contour on the underside. In positioning, the measurement device is on a flat surface here and the cassette is pushed under the measurement device laterally. Here, the wings serve centring and indicate the direction in which the test is positioned for the user.

Figure 6:
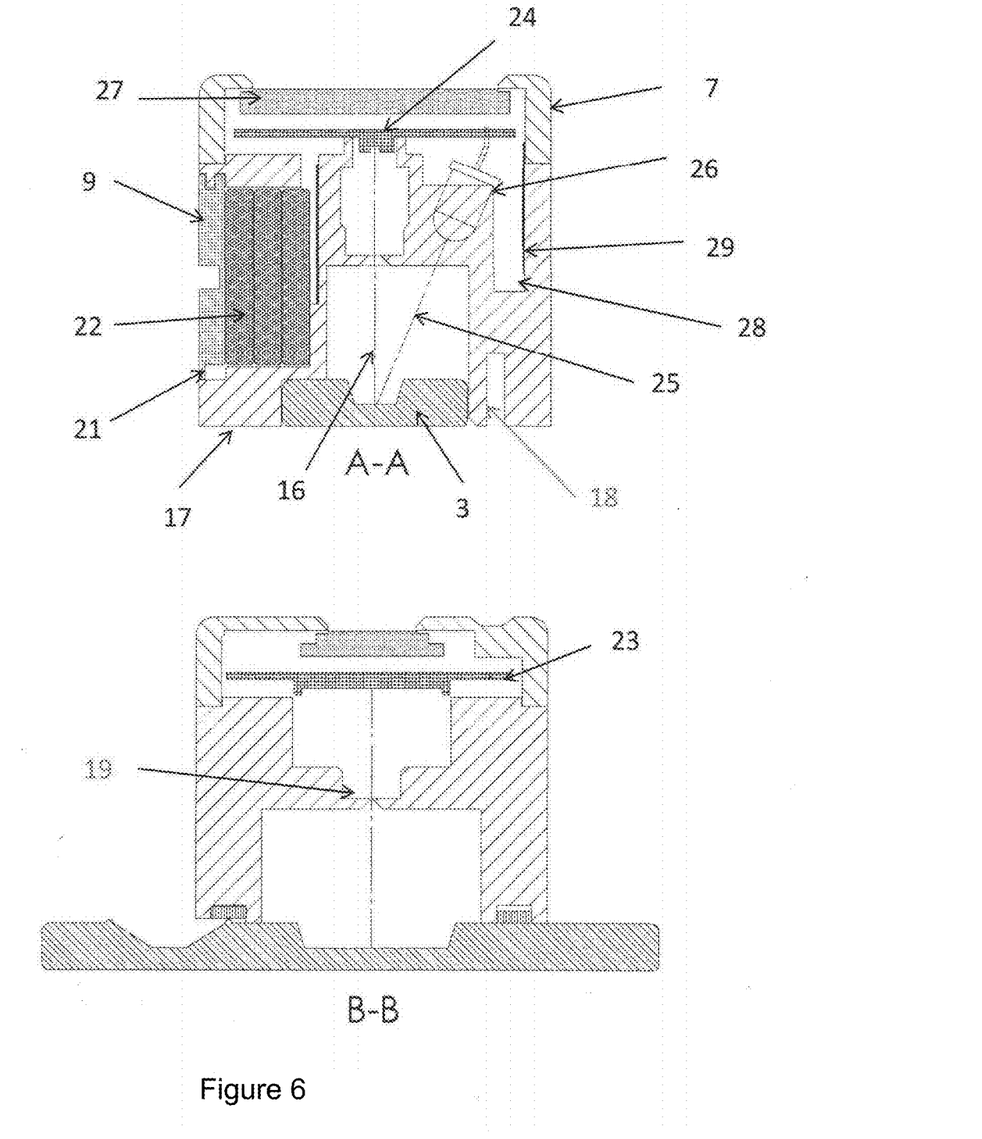
FIGS. 6 and 6a: section through the measurement device

FIG. 6 shows two sections through the measurement device at right angles to one another. The axis of the optical imaging (16) runs vertical to the underside of the reading aid (17). In the centre of the body, there is an aperture with a slot-shaped opening (19), which can be inserted directly into the housing in the manufacturing process (preferably in injection molding), with the result that no part to be assembled additionally is necessary. The slot aperture comprises a funnel-shaped opening, which, in a beneficial embodiment, manifests a width and length optimal for the imaging at its narrowest point. The angle of the funnel has been chosen such that no light of the imaging is shadowed.

The basic body manifests a recess which acts as a battery compartment (21). In it, preferably 3 lithium cells (22) are inserted and electrically contacted. The battery compartment has been closed with the lid (9).

Above the optic, an electrical wiring carrier (23), preferably a circuit board, has been provided, on which the reception element (24), a CCD reception line (or matrix) has been fitted. On this circuit board, there are also elements which have not been portrayed, for example a microcontroller, the jack for the interface cable, the transmission/reception unit for the cable/contact-free data transmission and the switch. The circuit board is also used to actuate the source of light (26) with a cast-on lens cap.

This illumination is angled in its optical axis (25) and has been fitted in a housing contour in the basic part, with the result that the lighting taper optimally illuminates the light aperture (3) of the cassette (30). The optical axis of the source of light/LED (26) and its angle of inclination to the optical axis (16) have been selected such that no reflections can go from the observation window to the receiver.

The circuit board also contains conductors, the layouts of which have preferably been designed such that they are suited as transmission/reception units for the automatic and contact-free test identification with the help of electromagnetic waves (preferably RFID: Radio Frequency Identification). The layout of the conductors has not been portrayed here.

On the upper side of the added part (7), a display (27) has been fitted. The display is actuated via an electrical connection, not portrayed in the diagram.

Further, a signal transmitter (29) can have been fitted in the housing in the housing recess of the basic body (28).

The distance between aperture (19) or lens and the level to be detected on the test strip in the measurement field of the cassette, the focal distance of the lens or the diameter of the aperture and the distance from the level of the receiver element have been dimensioned such that the optical imaging conditions have been fulfilled. In particular, the aperture has been optimised with a view to light strength, diffraction and distortion. In a preferential embodiment, the aperture manifests a width of 0.2 mm and a length of more than 0.2 mm, in a beneficial embodiment a length of 0.75 mm.

In the area of the underside of the measurement device (17) there is the flexible tongue (18), which has been dimensioned such that it pushes the cassette against the opposite wall when contacting the test cassette (3). This means that the test cassette always pushes against a fixed stop. In this way, inlay tolerances in a dimension can be ruled out and the measurement reproducibility can be increased.

Figure 6A:
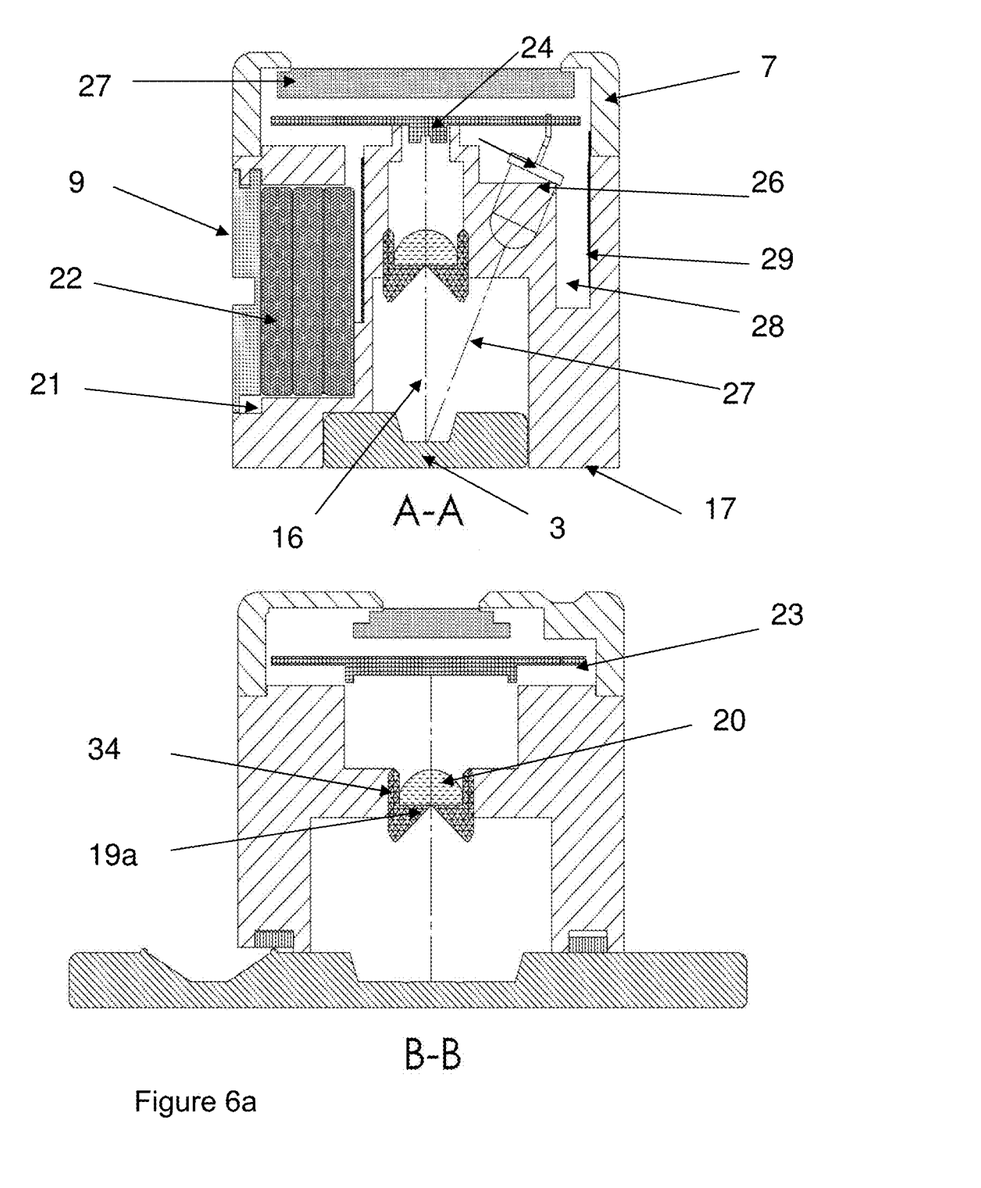

FIG. 6a alternatively shows a measurement device, in which an aperture (19a) has been arranged in a separate aperture body (34). In a particular embodiment, an additional lens (20) can have been arranged on the aperture body.

Figure 7:
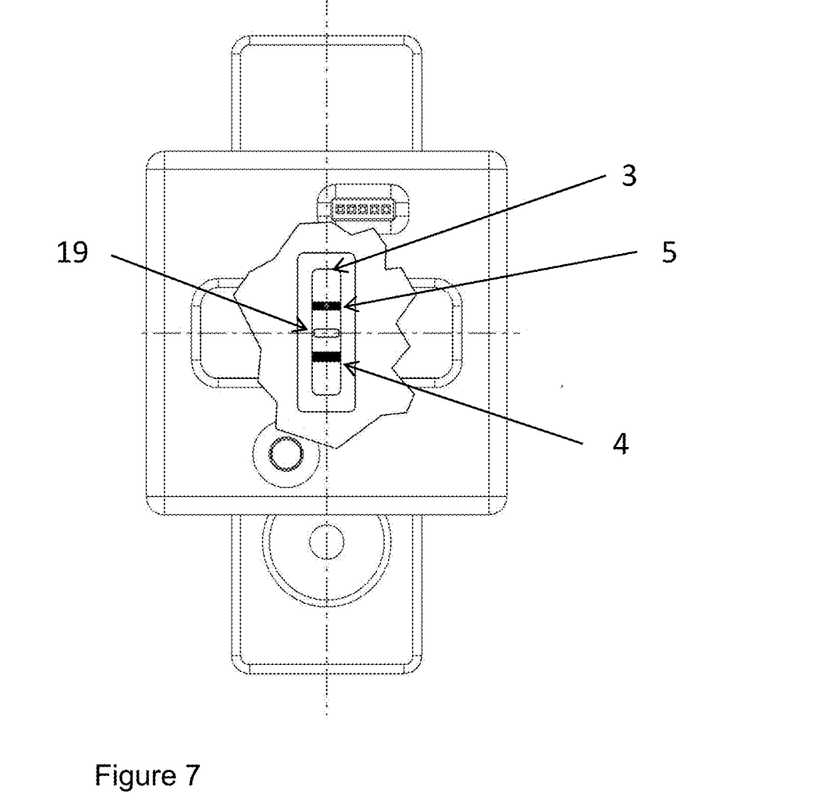
FIG. 7: section from the measurement device in a top view

FIG. 7 shows the top view onto the reading aid with a central section through the level of the aperture onto the level of the test. The section (3) for the test evaluation with control line (5) and test line (4) can be seen. Further, the pinhole aperture with the slot-shaped opening (19) has been portrayed on a parallel level above it. The slot-shaped imaging only improves the evaluation signal on the CCD if the longer side of the slot is as parallel as possible to the test and control line. The angle deviation should not be more than 5°.

Figure 8:
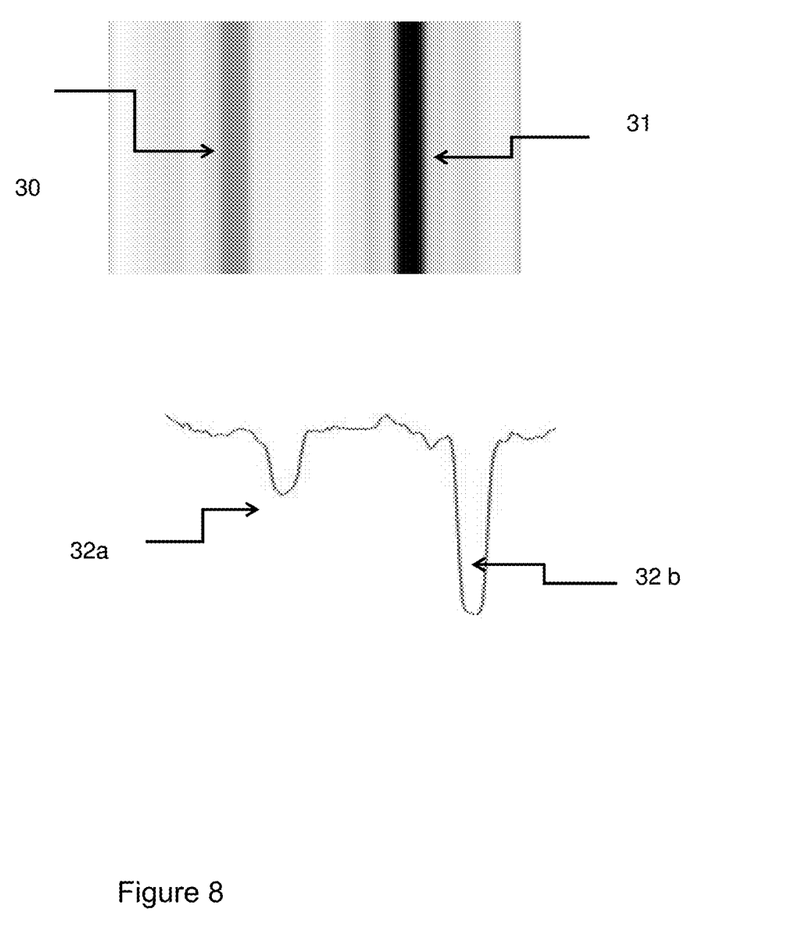
FIG. 8: recording of a test strip

FIG. 8 shows a scan recorded with such an arrangement according to the invention: trials have shown that the imaging with the set-up according to the invention leads to achievement of results which can be evaluated well. The scan was obtained similar to the principle of the "Camera Obscura" i.e. with an aperture as the imaging element. FIG. 9 further shows that barcodes can also be evaluated according to the same principle.

The measurement sequences is as follows:

In the aforementioned mode of procedure, the user positions the measurement device above the test cassette such that the optical imaging axis is central above the observation window of the cassette. He triggers the switch and thus starts the measurement process, controlled by the microcontroller. To start with, the illumination/LED is powered with impulses, it illuminates the test field with the test and control lines to be measured. The light, which is reflected diffusely, passes through the aperture and, if applicable, the lens onto the CCD with individual photosensitive elements. The image information is read out by the microcontroller, processed and displayed. For this, the measured values are compared with the values stored in the microcontroller and output. If applicable, the end of the measurement process is signalised by audible alarm and the result is displayed. The measured values are stored in a memory. The values can be read out and transmitted to an external computer with a specific data cable.

In order to be able to observe the test dynamism, that it to say the test during the development, measurement processes can be repeated at an arbitrary frequency. In addition, measurement errors can be reduced or ruled out as a result of multiple measurements.

FIG. 8 shows a profile recorded with such an optical imaging without a lens. The signal from the test line (30) and the control line (31) are clear. In the diagram, the grey level figures read out from the CCD are portrayed as a diagram, the peak height (32a) shows the grey level of the test line (30) and the peak height (32b) the grey level of the control line (31). The grey level of the test line can be compared with a calibrated figure stored in the device and displayed. These figures can be compared by the evaluation logic either with the absolute figures stored in the memory or with comparative values measured beforehand. It is also possible that the result from the ratio of the grey levels of both lines to one another is calculated. The configuration can be loaded directly before the measurement (preferably by means of RFID).

In FIG. 9, the image and the grey level scan for a barcode have been shown. It is surprising to see that maxima and minima can be clearly recognised with the measurement device and its camera. Therefore, barcodes can be recognised with the measurement device according to the invention. For example, this is sensible if the test manifests a barcode on the reverse for identification. In addition, calibration data for the test can be encrypted by the barcode.

Figure 10:
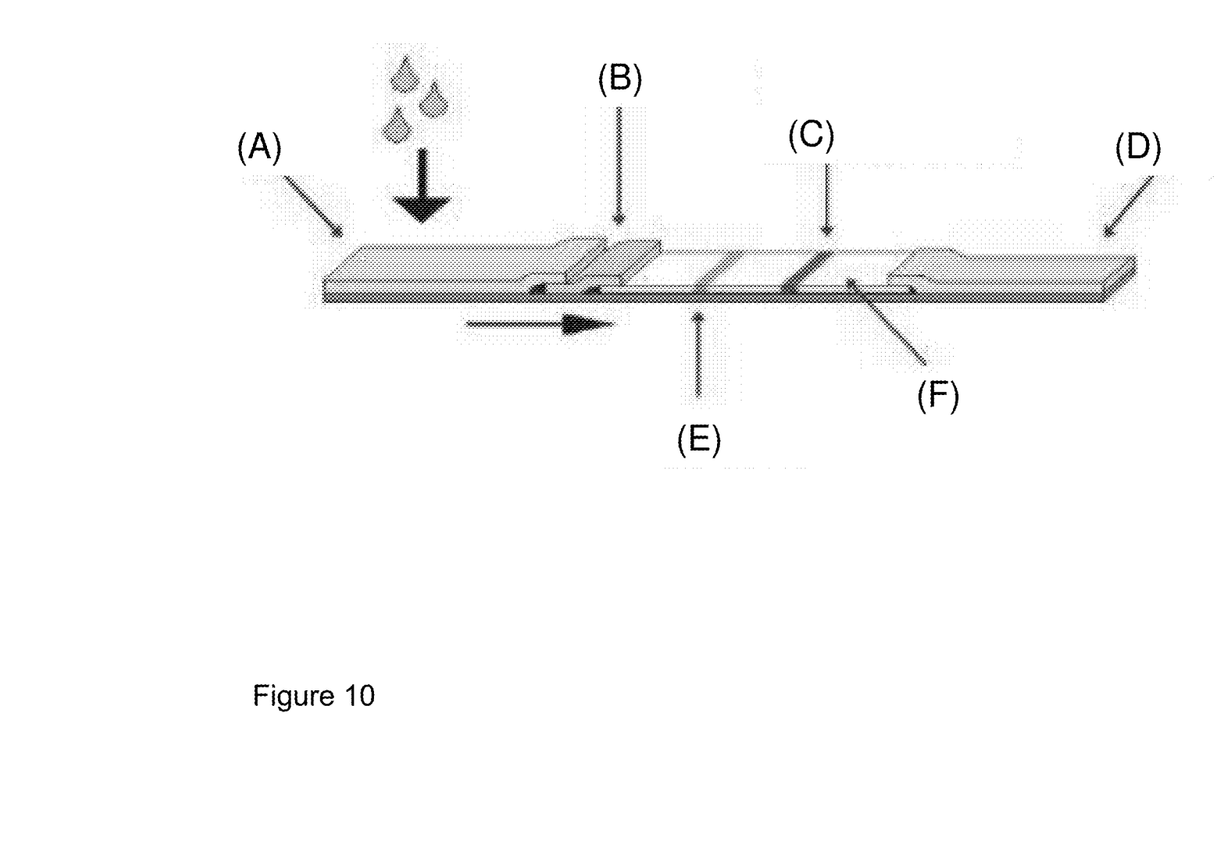

FIG. 10 shows the schematic set-up of an LFA.

Figure 11A:
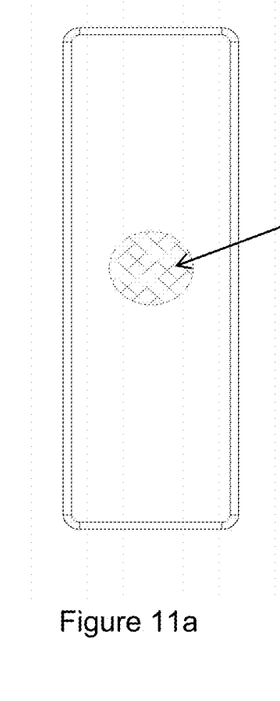
Figure 11B:
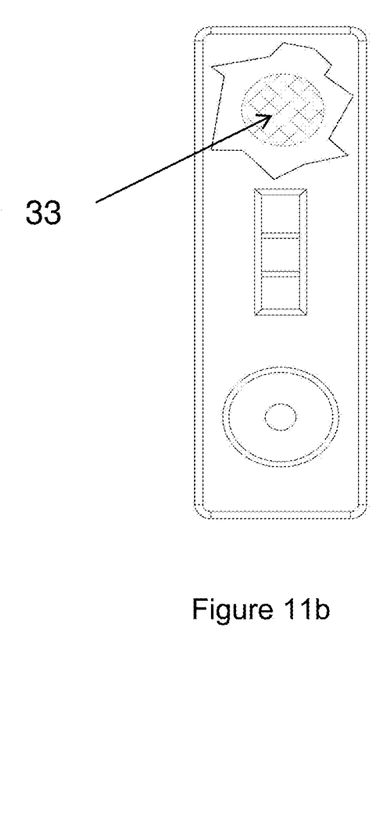

FIG. 11 shows a test cassette in the embodiment in which it has been provided with a transponder. In FIG. 11a, the transponder has been attached on the back, in FIG. 11b, the transponder has been integrated between the upper and lower shell of the cassette. The transponder contains the test-specific calibration and configuration data, which are inquired by the device electronics before the start of the measurement and are transmitted wirelessly.

Following the measurement, the data/results obtained can be stored in the transponder. This kind of test is here further referred to as "smart test".

A "smart test" is a quick test in which the necessary data for the test evaluation have been inserted and can be accessed for the evaluation, preferably (here) by means of an RFID chip/RFID tag. With the help of this arrangement, the situation that wrong data for the test to be measured can be put into the reading device by the user will be avoided.

Depositing the data/results obtained in the RFID tag after the evaluation is imaginable. Thus, it is possible to provide the data, for example, for the physician giving treatment or the user's carer for later use and documentation. Thus, the user is placed in a position to do the test independently and to archive the unadulterated data which are obtained for later use.

In order to make further use of the data, merely a reading device that can evaluate RFID tags is necessary (for example, a Smartphone with matching software (application)).

The invention claimed is:

1. A device for digital evaluation for quick tests, comprising: a housing body, and an added part, said housing body and said added part containing a source of light, optical components for optical imaging, a CCD line as a reception element for receiving an image of a quick test cassette placed in said device, an electronic circuit on a circuit board for receiving data from said reception element, a display component, an electrical interface for data transmission, an opening for insertion of the quick test cassette, a battery compartment with batteries and an operating element, said operating element being a switch: and a transmission/reception unit for contact-free loading and storage of information, wherein:

the optical components for the optical imaging comprise a pinhole aperture with a slot-shaped opening, arranged such that the slot is parallel to a control line and a test line-on the quick test cassette and wherein the pinhole aperture with the slot-shaped opening is integrated into the housing body, the electrical interface comprises an electrical wiring carrier, said circuit board is configured to read test-specific data in from a transponder on the quick test cassette or packaging of said quick test cassette automatically and contact-free through electromagnetic waves, and the light source comprises two LEDs integrated into the housing body configured for illumination of a test field.

2. The device of claim 1, wherein the slot has a width of 0.1 to 0.5 mm and the slot length is longer by a factor of 4.

3. The device of claim 1, wherein the light source is configured to adapt a wavelength of light emitted therefrom for the quick test cassette.

4. The device of claim 1, wherein an inner surface of the housing body is optically inactive.

5. The device of claim 1, wherein the illumination is done at an angle to the quick test cassette without disturbing reflections.

6. The device of claim 1, wherein the housing body comprises a recess configured as a positioning aid for protection against displacement or distortion of the quick test cassette.

7. The device of claim 1, wherein the housing body comprises a flexible tongue configured to press the quick test cassette against a fixed stop on the housing body.

8. The device of claim 1, wherein the transmission/reception unit is an RFD device.

9. A device for digital evaluation for quick tests; comprising: housing body, an added part, a source of light, optical components for optical imaging; a CCD line as a reception element, an electronic circuit on a circuit board, a display, component, an electrical interface for data transmission, an opening for insertion of a quick test sample, a battery compartment with batteries and an operating element, said operating element being a switch: and a transmission/reception unit for contact-free loading and storage of information, wherein:

the optical corn orients for the optical imaging comprises a pinhole aperture with a slot-shaped opening, arranged such that the slot is parallel to a control line and a test line for the quick test and wherein the pinhole aperture with the slot-shaped opening is integrated into the housing body, the electrical interface comprises an electrical wiring carrier, the light source comprises two LEDs integrated into the housing body configured for illumination of a test field, wherein the areas located inside the housing body have been matted.

10. A device for digital evaluation for quick tests, comprising: a housing body, an added part, a source of light, optical components for optical imaging, a CCD line as a reception element, an electronic circuit on a circuit board, a display component, an electrical interface for data transmission, an opening for insertion of a quick test sample, a supply battery compartment with batteries and an operating element, said operating element being a switch: and a transmission/reception unit for contact-free loading and storage of information, wherein:

the optical components for the optical imaging comprises a pinhole aperture with a slot-shaped opening, arranged such that the slot is parallel to a control line and a test line for the quick test and wherein the pinhole aperture with the slot-shaped opening is integrated into the housing body, the housing body comprises a flexible tongue configured to press the test sample against a fixed stop on the housing.

* * * * *